United States Patent
Christoforidis et al.

(10) Patent No.: US 11,744,908 B2
(45) Date of Patent: Sep. 5, 2023

(54) METHODS FOR DETERMINING BIODISTRIBUTION OF INTRAVITREAL ADMINISTERED MEDICAMENTS

(71) Applicants: John Christoforidis, Tucson, AZ (US); Michael Knopp, Columbus, OH (US)

(72) Inventors: John Christoforidis, Tucson, AZ (US); Michael Knopp, Columbus, OH (US)

(*) Notice: Subject to any disclaimer, the term of this patent is extended or adjusted under 35 U.S.C. 154(b) by 425 days.

(21) Appl. No.: 16/663,190

(22) Filed: Oct. 24, 2019

(65) Prior Publication Data

US 2020/0129647 A1    Apr. 30, 2020

Related U.S. Application Data

(60) Provisional application No. 62/750,481, filed on Oct. 25, 2018.

(51) Int. Cl.
*A61K 51/10*    (2006.01)
*A61B 6/00*    (2006.01)

(52) U.S. Cl.
CPC ........ *A61K 51/1021* (2013.01); *A61B 6/5235* (2013.01)

(58) Field of Classification Search
None
See application file for complete search history.

(56) References Cited

U.S. PATENT DOCUMENTS 9,833,523 B2    12/2017    Christoforidis et al.
2013/0295006 A1*    11/2013    Christoforidis .... A61K 51/1021
                                                          424/1.49

OTHER PUBLICATIONS

John T and Atwal ES. Pars plana approach can be used for surgical injection technique. Published Dec. 11, 2015. <healio.com/news/ophthalmology/20151211/pars-plana-approach-can-be-used-for-surgical-injection-technique>, accessed Dec. 18, 2021. 8 pages. (Year: 2015).*
Christoforidis, JB et al., "Systemic Biodistribution and Intravitreal Pharmacokinetic Properties of Bevacizumab, Ranibizumab, and Aflibercept in a Nonhuman Primate Model," Investigative Ophthalmology & Visual Science, Nov. 2017; 58:5636-5645.

* cited by examiner

*Primary Examiner* — Jennifer Chin
(74) *Attorney, Agent, or Firm* — Quarles & Brady, LLP; Yakov S. Sidorin

(57) ABSTRACT

Methods for determining systemic biodistribution characteristics of intravitrially administered medicaments. In some embodiments, radiolabeled agents or medicaments, such as I-124 labeled bevacizumab, ranibizumab and aflibercept, was imaged utilizing PET/CT in a non-human primate model, with radioactivity emission measurements made to determine the intravitreal half-lives of each agent and to determine the differences of radioactivity uptake in non-ocular organs.

12 Claims, 8 Drawing Sheets

METHODS FOR DETERMINING BIODISTRIBUTION OF INTRAVITREAL ADMINISTERED MEDICAMENTS

CROSS-REFERENCE TO RELATED APPLICATIONS

This application claims priority to U.S. Provisional Application Ser. No. 62/750,481, filed on Oct. 25, 2018, the contents of which hereby are incorporated by reference in its entirety.

STATEMENT REGARDING FEDERALLY SPONSORED RESEARCH

Not applicable.

BACKGROUND OF THE INVENTION

Anti-vascular endothelial growth factor (VEGF) agents such as bevacizumab (Avastin, Roche, Basel, Switzerland), ranibizumab (Lucentis, Roche, Basel, Switzerland) and aflibercept (Eylea, Regeneron, Tarrytown, N.Y., USA) have become the treatments of choice in the pharmacologic treatment of retinal neovascular disorders such as the exudative form of macular degeneration, macular edema from diabetic retinopathy and venous occlusions, and retinopathy of prematurity. Since their inception in 2005, the number of anti-VEGF injections in the United States has increased 10-20% annually. Intravitreal injection therapy of these agents is now the most commonly performed procedure in ophthalmology and it is estimated that over 6 million injections were performed in the United States in 2016 alone.

While certain pharmacokinetic have been determined, there is still a need for methods that can determine (e.g., through imaging) the systemic biodistribution of intravitreal administered medicaments such that side effects and other outcomes can be better understood.

SUMMARY OF INVENTION

Embodiments herein involve methods for determining systemic biodistribution characteristics of intravitrially administered medicaments.

In some embodiments, methods for determining the biodistribution of radiolabeled intravitreally-placed medicaments in a subject are described.

Methods described herein relate to intraocular placement of a radiolabeled medicament into the vitreous cavity through the pars plana of the subject performing positron emission tomography (PET) imaging of radioactive emission of subject's eyes and one or more extraocular organs.

In some embodiments, I-124 labeled bevacizumab, ranibizumab and aflibercept are imaged utilizing PET/CT in a non-human primate model, with radioactivity emission measurements made to determine the intravitreal half-lives of each agent and to determine the differences of radioactivity uptake in non-ocular organs.

These and other aspects are described in further detail below. However, the disclosure herein is not intended to be limited to specific embodiments or examples.

DETAILED DESCRIPTION

Figure 1:
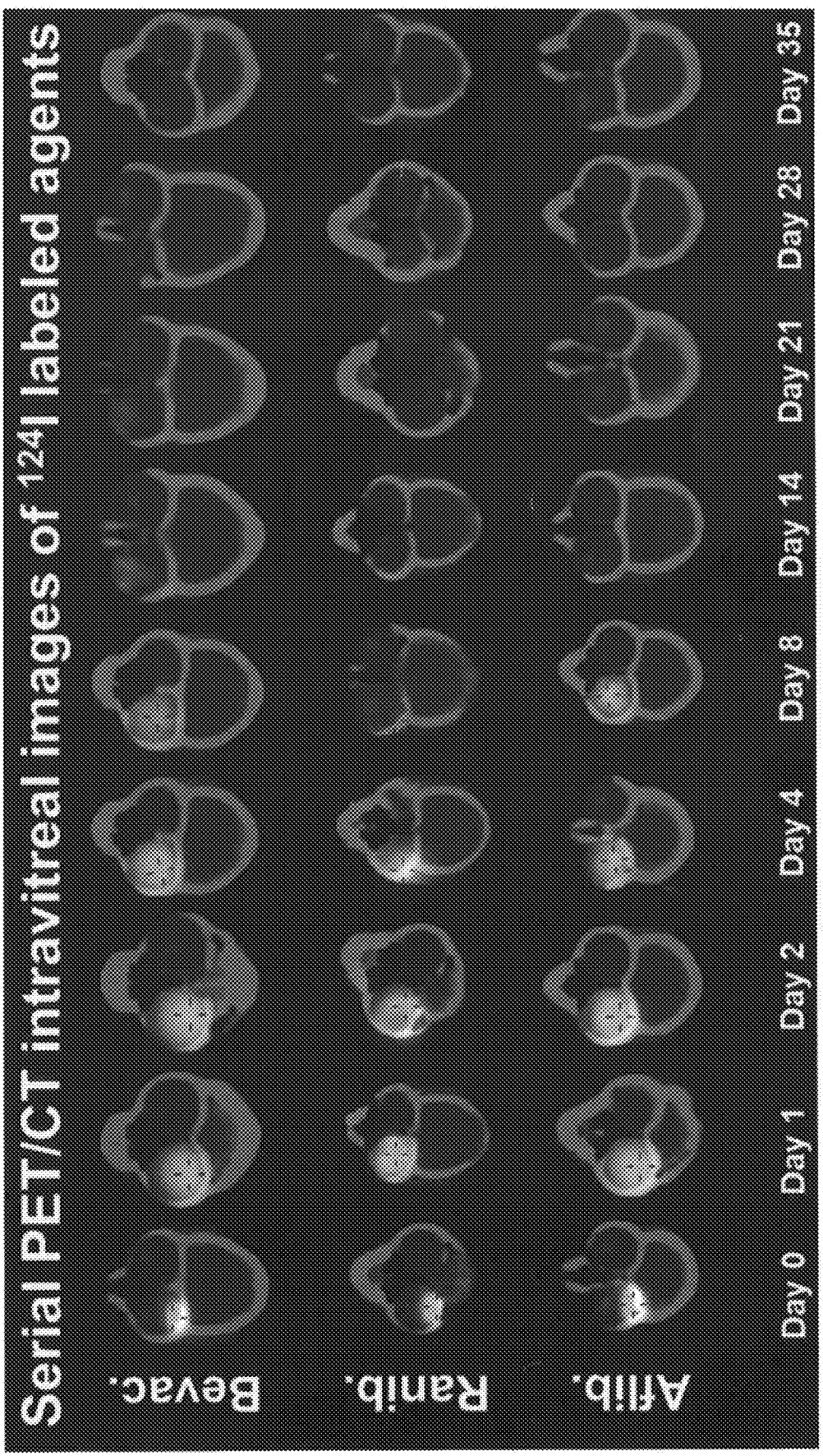
FIG. 1. Serial image montage illustrating clearance patterns of I-124 bevacizumab (top), I-124 ranibizumab (middle) and I-124 aflibercept (bottom) in an owl monkey model. I-124 bevacizumab was discernible until day 21 and detectable until day 28, while I-124 ranibizumab and I-124 aflibercept were visible until day 14 and detectable until day 21.

The preferred embodiments are described with reference to the Figures, in which like numbers represent the same or similar elements. The described features, structures, or characteristics of the invention may be combined in any suitable manner in one or more embodiments. In the following description, numerous specific details are recited to provide a thorough understanding of embodiments disclosed herein. One skilled in the relevant art will recognize, however, that embodiments disclosed herein may be practiced without one or more of the specific details, or with other methods, components, materials, and so forth. In other instances, well-known structures, materials, or operations are not shown or described in detail to avoid obscuring inventive aspects. As used herein, the term "drug" is an example of a medicament. All publications recited herein are hereby incorporated by reference in their entirety.

The intravitreal anti-VEGF drugs in clinical use today are clear substances that cannot be visualized following injection. Radiolabeling these agents allows them to be imaged through their radioactive emission with positron emission tomography (PET) imaging. Compared to immunoassay methods, PET/CT allows the radiolabelled agents to be non-invasively visualized and their radioactive emission permits the study of their pharmacokinetic and some biodistribution properties. With 7-9 time points obtained per subject, a smaller number of subjects can be studied per treatment group to determine the pharmacokinetic characteristics of the therapeutic agent.

Previous reports on a rabbit model have successfully demonstrated that PET/CT can visualize I-124 bevacizumab, I-124 ranibizumab and I-124 aflibercept in the vitreous cavity and can determine their pharmacokinetic properties. In these previous studies, the intravitreal half-lives for bevacizumab and ranibizumab were 4.2 and 2.8 days respectively comparing favorably with previous reports using immunoassay methodologies in a similar rabbit model.

Systemic biodistribution following systemic administration I-124 radiolabeled agents has been previously reported. However, to our knowledge, the systemic biodistribution of intravitreally placed therapeutic agents has not been previously examined. Recent advances in PET technology have significantly improved image resolution and allowed for more precise quantification of radioactive emission measurements of tagged agents. This has improved our ability to more accurately determine their intravitreal pharmacokinetic characteristics and to track their dissemination into extraocular organs. The non-human primate (NHP) model has inherent advantages over previously used rabbit models including a human-like proportioned vitreous cavity and lens, and the presence of a macula critical for binocular vision and stereopsis. These anatomic similarities can provide a more accurate assessment of intravitreally placed drugs for human use.

In certain embodiments, high resolution digital PET/CT (dPET/CT) is used to study the intravitreal pharmacokinetic properties and systemic biodistribution characteristics of I-124 labeled medicaments such as bevacizumab, ranibizumab and aflibercept after intravitreal placement in a non-human primate model.

Certain endpoints are possible utilizing the inventive methods described herein: first, to determine the intravitreal pharmacokinetic properties of the 3 anti-VEGF agents by serial ocular imaging, second, to study the serum levels for each of the three agents after intravitreal injection, and third, to examine the systemic biodistribution of each agent by sequential whole body PET.

Examples

Materials and Methods

Radiolabeling of bevacizumab, ranibizumab and aflibercept with I-124 (IBA Molecular, Dulles, Va.) was completed using a modified Iodogen method.11 Radiochemical purities for I-124 bevacizumab, I-124 ranibizumab and I-124 aflibercept were 96.2%, 96.2% and 96.6% respectively.

All treatments were conducted in agreement with the ARVO Statement for the Use of Animals in Ophthalmic and Vision Research. All experimental protocols were approved, and the procedures followed were in accordance with the ethical standards of the Institutional Animal Care and Use Committee (IACUC) at The Ohio State University. Twelve (7 male and 5 female) adult *Aotus trivirgatus* known as owl monkeys (Keeling Center for Comparative Medicine and Research at The University of Texas MD Anderson Cancer Center, Bastrop, Tex.) weighing 940-1150 grams were used for this study. Under general anesthesia, three groups of 4 owl monkeys each underwent intravitreal injection. 1.25 mg/0.05 mL I-124 bevacizumab (2 female, 2 male), 0.5 mg/0.05 mL I-124 ranibizumab (2 female, 2 male) or 2.0 mg/0.05 mL I-124 aflibercept (1 female, 3 male) was placed 1.5 mm posterior to the limbus using a 32 gauge needle in the right eye of each of the twelve subjects.

Immediately following intravitreal injection on day 0, each subject underwent dPET/CT imaging (Vereos, Philips Healthcare, Andover, Mass.) and sequential imaging was performed on days 1, 2, 4, 8, 14, 21, 28 and 35. At each time point, two bed position acquisitions to cover the head and body of the NHPs were obtained. All dPET images were reconstructed using 2 mm voxel length. Serums were collected at post-intravitreal injection hours 1, 2, 4, 8, 12 and days 1, 2, 4, 8, 14, 21, 28 and 35. Between 1.0 and 1.5 mL of blood from the femoral artery was collected in BD Vacutainer® Plus plastic serum tubes with 5.0 mL Gold BD Hemogard™ closure venous blood collection tubes (BD, Franklin Lakes, N.J.). Radioactive emission levels from the collected blood samples were then measured with a gamma counter (WIZARD2® Automatic Gamma Counter, Perkin Elmer Inc., Waltham, Mass.). The collected blood was then centrifuged at 3500 rpm for 5 minutes (Adams Physicians Compact Centrifuge, Clay Adams, Parsippany, N.J.) and the separated serum was collected using 7 ml polyethylene LabAid transfer pipettes (Biomed Resource, Inc., Riverside Calif.) and placed into polypropylene 1.5 mL tubes (Heathrow Scientific LLC, Vernon Hill, Ill.). At the completion of the study, the subjects were quarantined to allow for 10 half-lives of I-124 radioactivity decay following intravitreal injection (42 days or 1 week after the last imaging session) before being released.

The radioactive units (Bq/mL) were corrected to account for I-124 radioactive decay which has a physical half-life of 4.18 days. Clearance curves were then formulated with the resulting measurements and the intravitreal half-life for each subject was calculated using a formula to describe first order kinetics below:

$$T^{1/2} = \frac{T \times \log 2}{\log[\text{Drug}]_b / [\text{Drug}]_e}$$

Whereby: $T_{1/2}$=Half Life
T=Elapsed Time
$[\text{Drug}]_b$=Beginning Amount
$[\text{Drug}]_e$=Ending Amount To study the biodistribution patterns of each agent after intravitreal injection, PET/CT images of specific organs were examined. In addition to the injected right eye, eleven other organs that exhibited radioactive uptake were examined and compared for each of the 3 agents. The examined organs were the contralateral left eye, right and left thyroid lobes, right and left kidneys, bladder, spleen, right and left distal femur bones, heart and liver. The regions of interest (ROI) for each tissue type were held constant for all imaging sessions and all analysis was performed using Philips software. Mean standardized uptake values (SUV) values were determined as a function of post injection time for each antibody tested. The SUV scales were adjusted to lower emission thresholds to allow for better visualization of organs with lower radioactivity levels.

Statistical analysis was performed to compare differences in the 3 treatment groups with one-way analysis of variance (ANOVA) with post-hoc Tukey HSD Test for multiple comparisons to adjust for multiple hypothesis tests and statistical significance was set at p<0.05. Means and standard errors were calculated for each treatment at each time. All analyses were performed using SAS/STAT software, Version 9.4 (SAS Institute Inc., Cary, N.C., USA).

Results:

1. Intravitreal Anatomic and Pharmacokinetic Properties

During the course of the study, none of the eyes developed adverse events such as endophthalmitis, uveitis or cataract. The montage in FIG. 1 illustrates serial images for three subjects one for each of the 3 agents. I-124 bevacizumab was visible until day 21 while both I-124 ranibizumab and I-124 aflibercept were visible until day 14. Intravitreal levels of radioactivity (Bq/mL) are listed for each subject in Table 1.

able in the vitreous cavity until day 30, average I-124 ranibizumab until day 22, and average I-124 aflibercept until day 21. The average clearance half-lives with standard error and 95% confidence intervals after correction for radioactive decay were found to be 3.60±0.20 (3.40, 3.79) days for bevacizumab, 2.73±0.19 (2.55, 2.92) days for ranibizumab, and 2.44±0.32 (2.12, 2.76) days for aflibercept. The difference was significantly higher for I-124 bevacizumab than both other agents (p<0.05) and the calculated half-lives were not significantly different between ranibizumab and aflibercept.

The drug retention rates were found to trend higher for the females in each of the agent groups. The average intravitreal half-lives were 3.73 days for females and 3.46 days for

TABLE 1

Intravitreal radioactivity levels (Bq/ml)

| Sex Day | F Lucentis | M Lucentis | F Lucentis | M Lucentis | F Avastin | M Avastin | F Avastin | M Avastin | F Eylea | M Eylea | M Eylea | M Eylea |
|---|---|---|---|---|---|---|---|---|---|---|---|---|
| 0 | 1238176 | 2226348 | 1544988 | 2361806 | 4924195 | 5238554 | 1853140 | 2895941 | 1575156 | 1098949 | 1119739 | 1225421 |
| 1 | 910799 | 510882 | 630789 | 320859 | 1568718 | 996153 | 1441724 | 1541633 | 1071211 | 518112 | 608523 | 676933 |
| 2 | 430081 | 186467 | 305297 | 103681 | 851048 | 496990 | 762783 | 912302 | 399504 | 238891 | 194961 | 483031 |
| 4 | 65708 | 27162 | 37218 | 16983 | 260490 | 129286 | 163401 | 217691 | 109959 | 49172.2 | 14254.5 | 109452 |
| 8 | 8633 | 1638 | 3575 | 1230 | 21918 | 9910 | 15320 | 13752 | 9356 | 3072 | 2866 | 10317 |
| 14 | 456 | 238 | 222 | 111 | 1339 | 1043 | 963 | 1803 | 290 | 72 | 295 | 364 |
| 21 | 82 | 45 | 44 | 13 | 249 | 137 | 404 | 161 | 51 | 4 | 46 | 15 |
| 28 | 30 | 16 | 13 | 5 | 52 | 28 | 144 | 50 | 34 | 0 | 1 | 12 |
| 35 | 3 | 2 | 0 | 0 | 13 | 6 | 1 | 15 | 0 | 0 | 0 | 0 |

Table 1. Listing of intravitreal radioactivity levels (Bq/ml) for each of the 3 agents at each time point. Radioactivity levels below 30 Bq/ml were considered to be compatible with background noise.

I-124 uptake in the thyroid lobules was visible on day 35 in all subjects indicating that the radioactivity clearance from the vitreous cavity was due to agent egress from the vitreous rather than I-124 radioactive decay.

The resulting clearance patterns for each agent fits a 2 phase curve with an initial rapid distribution phase until day 4 followed by a slower elimination phase from day 8 males in the I-124 bevacizumab group, 2.97 days for females and 2.49 days for males in the I-124 ranibizumab group, and 3.16 days for the single female and 2.12 days for the 3 males in the I-124 aflibercept group. The number of subjects per male and female group was too small for statistical considerations.

2. Drug Serum Levels

Table 2 lists the mean measured serum I-124 bevacizumab, I-124 aflibercept and I-124 ranibizumab levels with standard errors in gamma counter radioactivity counts at each time point.

TABLE 2

Labeled agent serum level means with standard errors and statistical comparisons.

Figure 2:
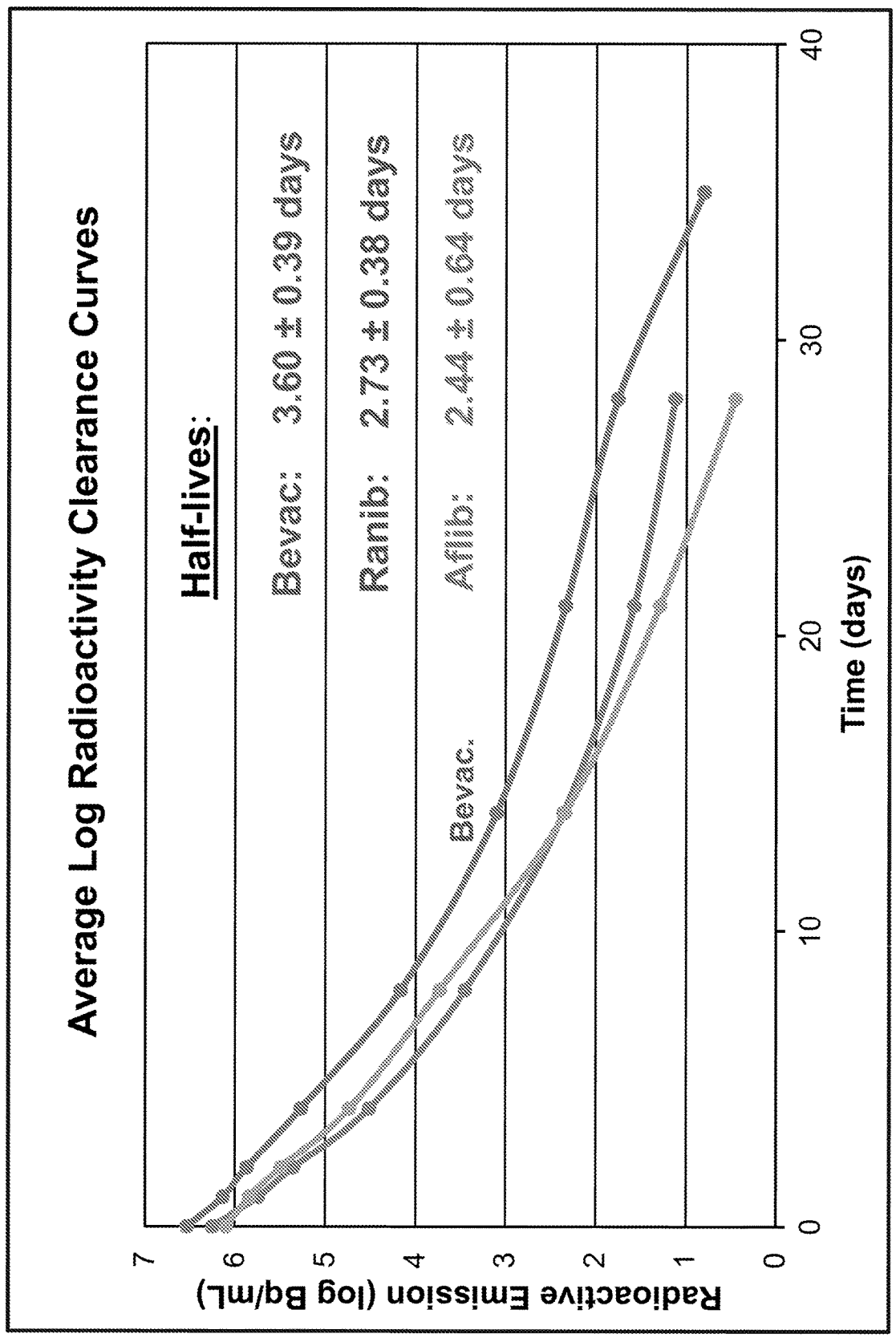
FIG. 2. Summary of the average logarithmic clearance curves of I-124 labelled aflibercept (green/bottom line at 28 days), bevacizumab (blue/top line) and ranibizumab (red/middle line at 28 days). I-124 bevacizumab had the longest half-life while I-124 aflibercept had the shortest.

| Hour | I-124 Bevacizumab | I-124 Aflibercept | I-124 Ranibizumab | p-value (Bev vs Afl) | p-value (Bev vs Ran) | p-value (Afl vs Ran) |
|---|---|---|---|---|---|---|
| 1 | 2647 ± 636 | 2443 ± 607 | 6163 ± 1733 | 0.991 | 0.122 | 0.100 |
| 2 | 7886 ± 1726 | 6694 ± 1344 | 9559 ± 906 | 0.815 | 0.674 | 0.344 |
| 4 | 37902 ± 12609 | 14826 ± 2048 | 16272 ± 3389 | 0.137 | 0.167 | 0.990 |
| 8 | 151810 ± 24126 | 28266 ± 3290 | 22636 ± 5922 | <0.001 | <0.001 | 0.959 |
| 12 | 192031 ± 12975 | 39266 ± 1090 | 54758 ± 11112 | <0.001 | <0.001 | 0.533 |
| 24 | 323202 ± 31799 | 90061 ± 10750 | 74466 ± 11561 | <0.001 | <0.001 | 0.855 |
| 48 | 409142 ± 29377 | 135845 ± 13826 | 60965 ± 8551 | <0.001 | <0.001 | 0.055 |
| 96 | 455267 ± 69745 | 82321 ± 13173 | 27103 ± 8368 | <0.001 | <0.001 | 0.623 |
| 192 | 241397 ± 31434 | 30209 ± 3222 | 7084 ± 1655 | <0.001 | <0.001 | 0.657 |
| 336 | 120908 ± 22026 | 13693 ± 2712 | 2585 ± 702 | <0.001 | <0.001 | 0.817 |
| 504 | 89300 ± 94328 | 9066 ± 1660 | 2006 ± 422 | <0.001 | <0.001 | 0.867 | onwards (FIG. 2). By graphic extrapolation of I-124 levels to the noise plane, average I-124 bevacizumab was detect Table 2. Comparison of mean serum I-124 bevacizumab, I-124 aflibercept and I-124 ranibizumab levels with standard errors (gamma counter counts) at each measured time point. Adjusted p-values for multiple comparisons reflect significant differences between I-124 bevacizumab and both other agents beginning at 8 hours post-injection. There were no significant differences in the serum levels between I-124 aflibercept and I-124 ranibizumab at any of the measured time points.

Figure 3:
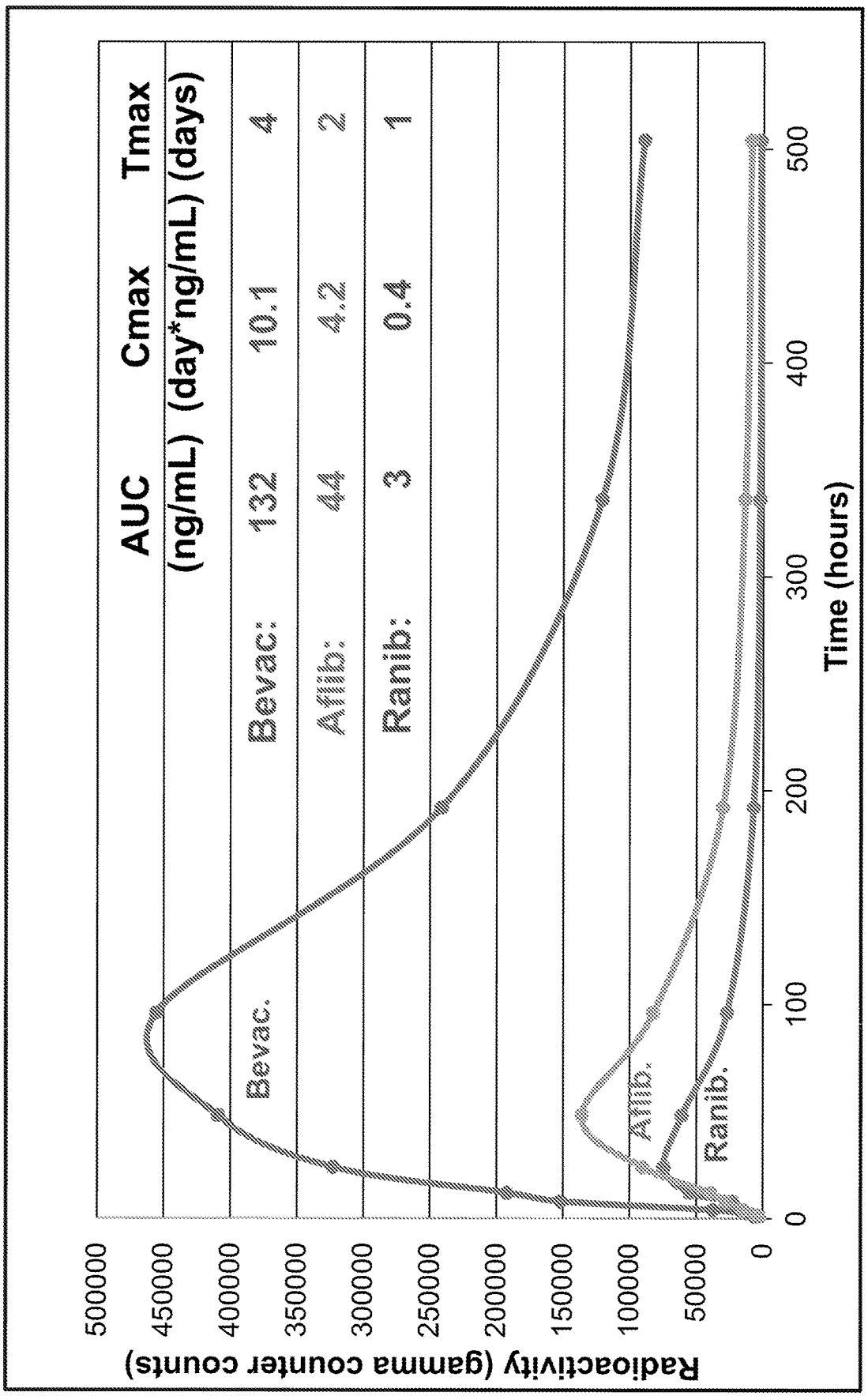
FIG. 3. Graphic representation of average serum clearance curves of 124I-labelled aflibercept (green/middle line), bevacizumab (blue/top line) and ranibizumab (red/bottom line). 124I-bevacizumab had significantly larger AUC, Cmax and Tmax when compared to the other 2 agents. There were no significant differences in the serum levels between I-124 aflibercept and I-124 ranibizumab at any of the measured time points.

The values are graphically represented in FIG. 3. There were no significant differences between the three drug levels up to 4 hours post-intravitreal injection. Beginning at 8 hours post-injection, I-124 bevacizumab levels measured significantly higher than the other two agents and they remained significant compared to both agents for the remainder of the study. No significant differences in the serum levels were found between I-124 aflibercept and I-124 ranibizumab at any of the measured time points. I-124 ranibizumab levels were measurable until day 4 and I-124 aflibercept until day 8, and both were compatible with background noise thereafter.

Table 3 summarizes the pharmacokinetic parameters for each treatment group.

lower for I-124 aflibercept (3.50±0.31 ng/mL) and least for I-124 ranibizumab (0.47±0.07 ng/mL). These differences were significantly higher for I-124 bevacizumab serum levels than both I-124 aflibercept and I-124 ranibizumab (p=0.038 and p=0.002 respectively) but they were not significantly higher for I-124 aflibercept when compared to I-124 ranibizumab (p=0.147).

The average time to maximal plasma concentration (Tmax) was earliest for the I-124 ranibizumab (24 hours), followed by I-124 aflibercept (48 hours) and I-124 bevacizumab (84 hours). The area under the curve (AUC) was greatest for I-124 bevacizumab (109.0±17.51 day*ng/mL) followed by I-124 aflibercept (38.63±3.76 day*ng/mL) and I-124 ranibizumab (2.79±0.55 day*ng/mL). AUC was significantly higher for I-124 bevacizumab than both I-124 aflibercept and I-124 ranibizumab (p=0.002 and p<0.001 respectively). The higher AUC for I-124 aflibercept compared to I-124 ranibizumab was not significant (p=0.085).

TABLE 3

Pharmacokinetic parameter means with SD for each treatment group

| Parameter | I-124 Bevaciz. | I-124 Aflib. | I-124 Ranibiz. | p-value (Bev vs Afl | p-value (Bev vs Ran) | p-value (Afl vs Ran) |
|---|---|---|---|---|---|---|
| Tmax (hours) | 84 ± 12 | 24 ± 0 | 48 ± 0 | 0.013* | 0.001* | 0.085 |
| Cmax (ng/mL) | 7.80 ± 1.75 | 3.50 ± 0.31 | 0.47 ± 0.07 | 0.038* | 0.002* | 0.147 |
| AUC (day * ng/mL) | 109.0 ± 17.51 | 38.63 ± 3.76 | 2.79 ± 0.55 | 0.002* | 0.001* | 0.085 |

*indicates statistical significance (p < 0.05)

Table 3. Listing of mean serum pharmacokinetic parameters with standard errors for the I-124 bevacizumab (Bev), I-124 aflibercept (Afl) and I-124 ranibizumab (Ran) groups. P-values were adjusted for multiple comparisons with p<0.05 set for statistical significance. The differences between I-124 bevacizumab and the other 2 agents were significant for Tmax, Cmax and AUC, while there were no significant differences for any of the parameters between I-124 aflibercept and I-124 ranibizumab.

Figure 4:
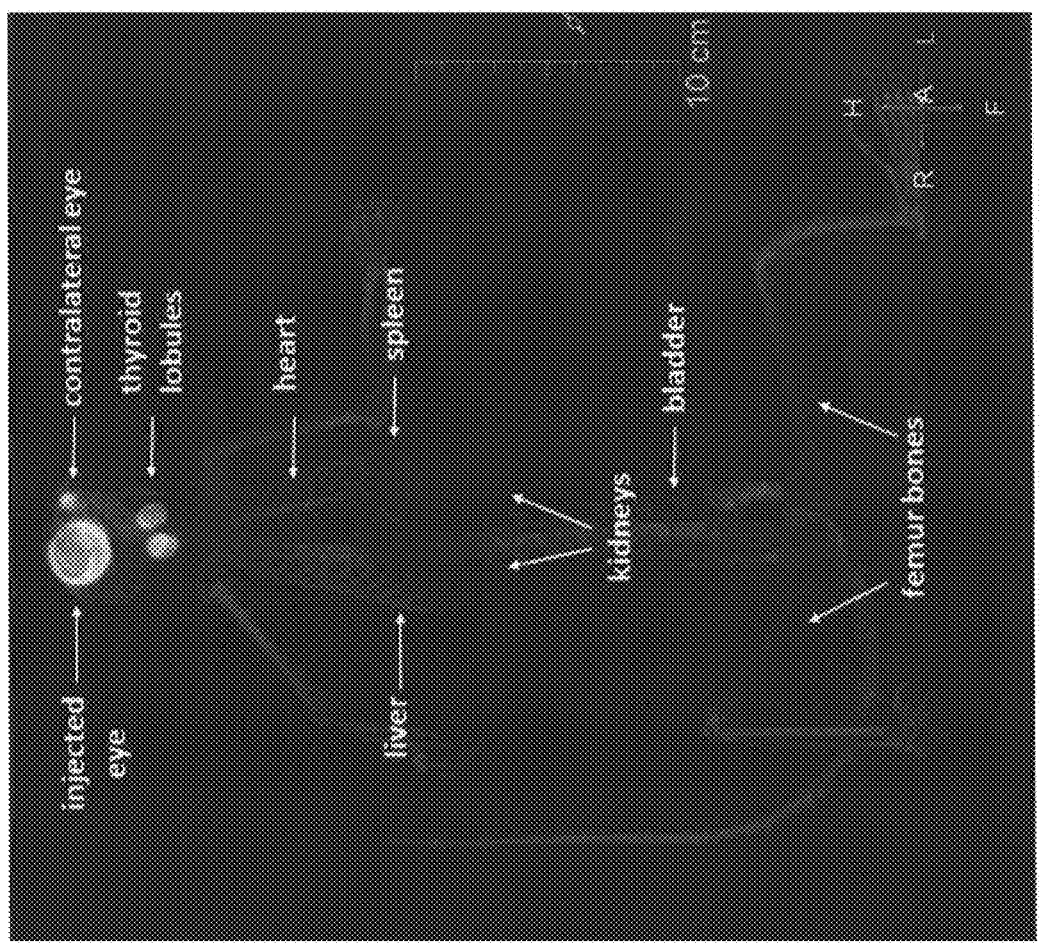
FIG. 4. Serial image montage illustrating the systemic biodistribution of I-124 bevacizumab (top), I-124 ranibizumab (middle) and I-124 aflibercept (bottom) in an owl monkey. Accumulations in the injected eye and both thyroid lobules were seen throughout the study while radioactivity could be detected in other organs until day 21. I-124 bevacizumab had the widest and most prolonged biodistribution among the 3 agents.
Figure 5:
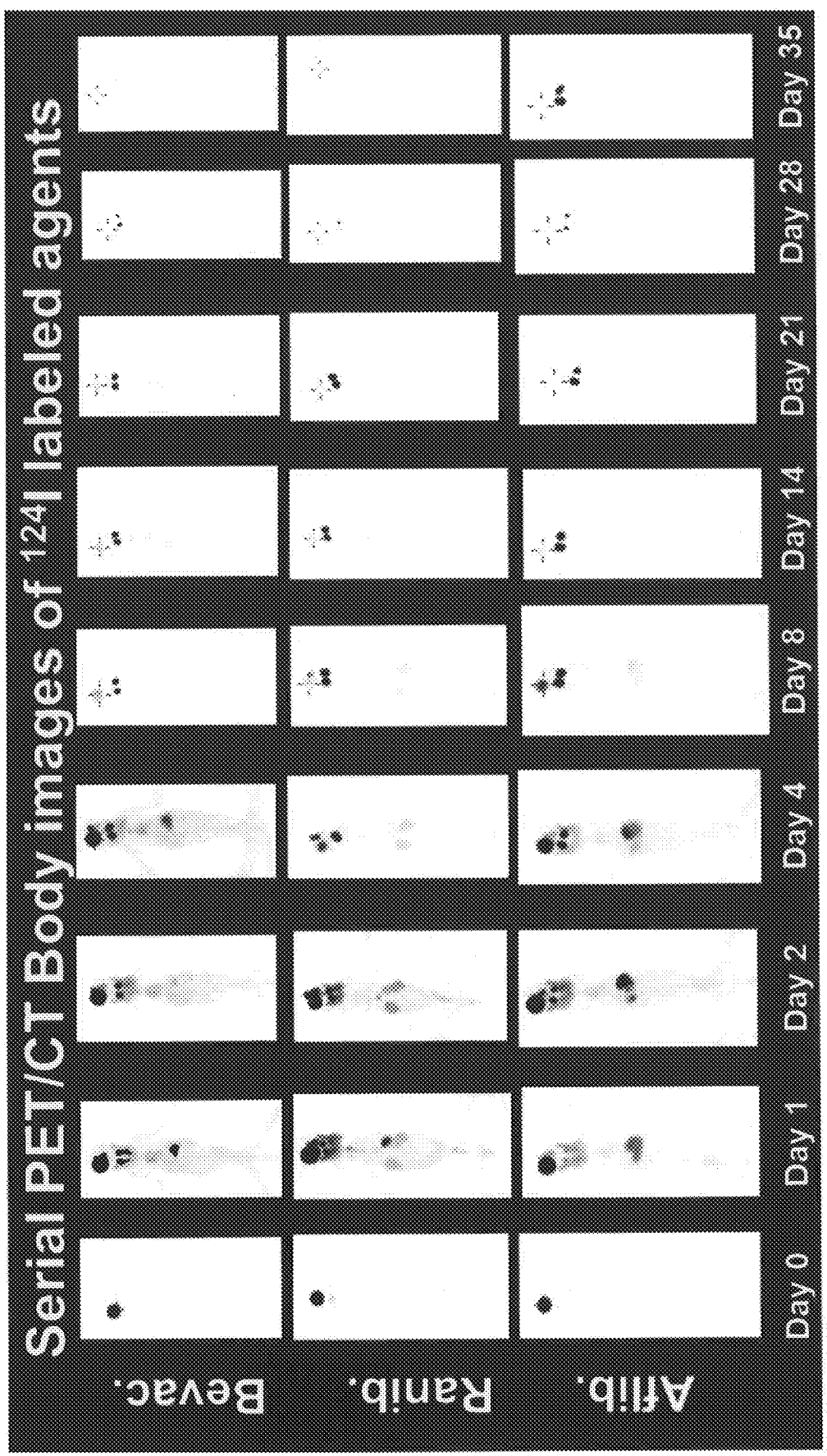
FIG. 5. Magnified PET/CT image of an I-124 bevacizumab-treated subject on day 4 depicting radioactivity uptake in various organs following intravitreal injection.
Figure 6:
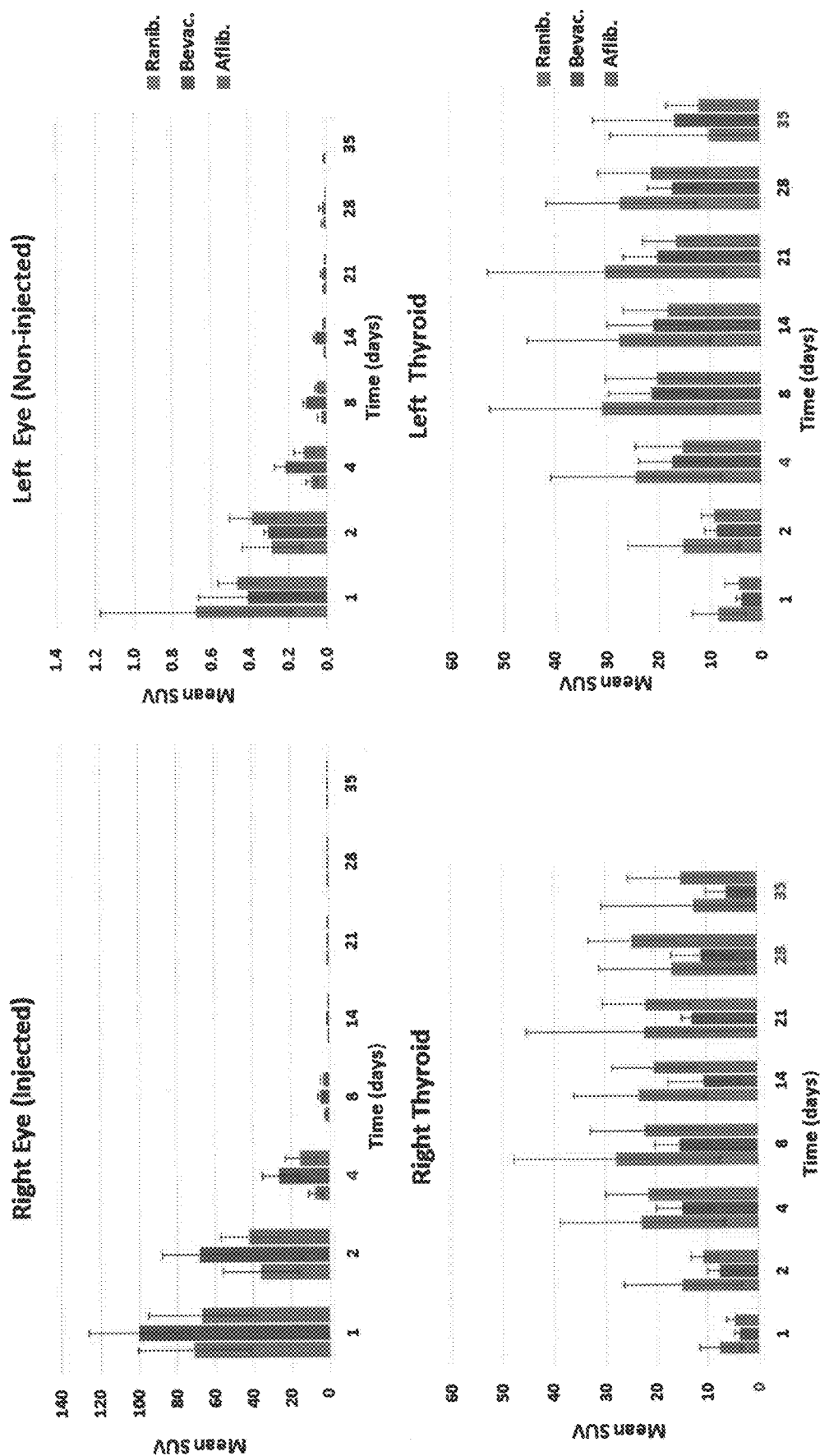
FIG. 6. Comparison of serial radioactivity uptake values with standard error bars in mean standardized uptake values (SUV) between the three anti-VEGF agents in the injected and non-injected eyes, and thyroid lobules (Ranib. first in each daily series, Bevac. second in each daily series, and Aflib. third in each daily series).
Figure 7:
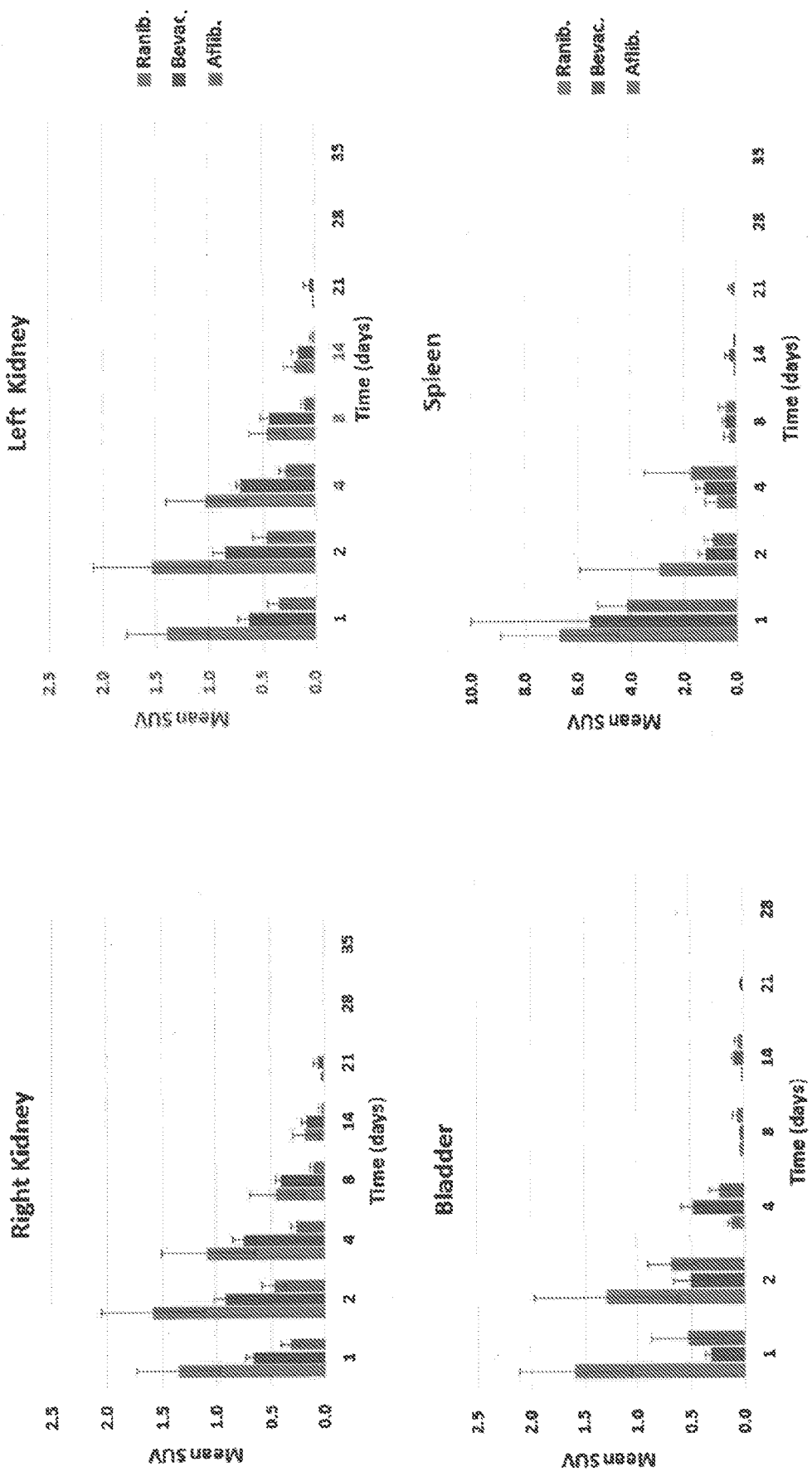
FIG. 7. Comparison of serial radioactivity uptake values with standard error bars in mean standardized uptake values (SUV) between the three anti-VEGF agents in both kidneys, bladder and spleen (Ranib. first in each daily series, Bevac. second in each daily series, and Aflib. third in each daily series).
Figure 8:
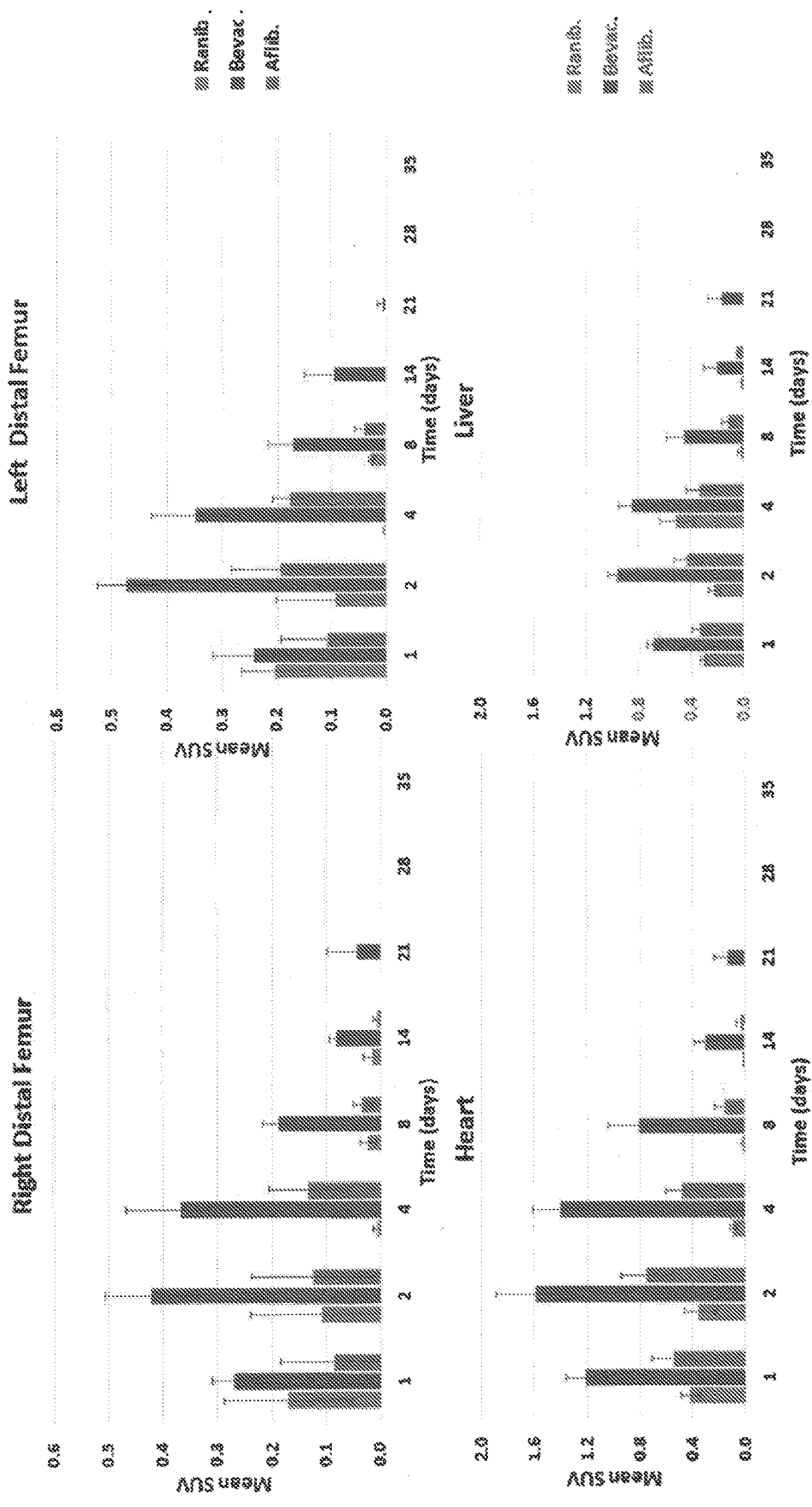
FIG. 8. Comparison of serial radioactivity uptake values with standard error bars in mean standardized uptake values (SUV) between the three anti-VEGF agents in both distal femurs, heart and liver (Ranib. first in each daily series, Bevac. second in each daily series, and Aflib. third in each daily series).

The average peak serum concentration (Cmax) was highest for the I-124 bevacizumab subjects (7.80±1.75 ng/mL), 3. Systemic Biodistribution FIG. 4 demonstrates three PET/CT montages for one subject from each of the 3 treatment groups and FIG. 5 is a magnified view of an I-124 bevacizumab subject on day 4 depicting the various organs with radioactivity uptake following intravitreal injection in greater detail. FIGS. 6-8 graphically represent the differences in biodistribution findings for each of the examined organs. Table 4 summarizes the p-values adjusted for multiple comparisons between the 3 treatment groups at each time point and for each studied organ.

TABLE 4

Statistical summary between the 3 treatment groups.

| Organ | Comparison | Day 0 | Day 1 | Day 2 | Day 4 | Day 8 | Day 14 | Day 21 | Day 28 | Day 35 |
|---|---|---|---|---|---|---|---|---|---|---|
| Right Eye | Ran. vs Bev. | 0.546 | 0.360 | 0.084 | 0.015* | 0.102 | 0.001* | 0.037* | 0.372 | 0.041* |
| | Ran. vs Afl. | 0.348 | 0.975 | 0.898 | 0.343 | 0.538 | 0.912 | 0.566 | 0.046* | 0.842 |
| | Bev. vs Afl. | 0.072 | 0.272 | 0.165 | 0.151 | 0.467 | 0.001* | 0.007* | 0.005* | 0.017* |
| Left Eye | Ran. vs Bev. | | 0.499 | 0.974 | 0.022* | <0.001* | <0.001* | 0.504 | 0.489 | 0.140 |
| | Ran. vs Afl. | | 0.636 | 0.443 | 0.569 | 0.131 | 0.365 | 0.921 | 0.659 | 0.140 |
| | Bev. vs Afl. | | 0.969 | 0.562 | 0.076 | 0.003* | 0.003* | 0.315 | 0.149 | 1.000 |
| Right Thyroid | Ran. vs Bev. | | 0.145 | 0.338 | 0.581 | 0.424 | 0.214 | 0.650 | 0.719 | 0.766 |
| | Ran. vs Afl. | | 0.297 | 0.685 | 0.984 | 0.833 | 0.904 | 1.000 | 0.606 | 0.957 |
| | Bev. vs Afl. | | 0.871 | 0.798 | 0.682 | 0.752 | 0.380 | 0.666 | 0.258 | 0.602 |
| Left Thyroid | Ran. vs Bev. | | 0.205 | 0.374 | 0.664 | 0.637 | 0.733 | 0.590 | 0.420 | 0.808 |
| | Ran. vs Afl. | | 0.266 | 0.423 | 0.533 | 0.579 | 0.550 | 0.399 | 0.758 | 0.970 |
| | Bev. vs Afl. | | 0.981 | 0.994 | 0.972 | 0.995 | 0.947 | 0.934 | 0.842 | 0.903 |
| Right Kidney | Ran. vs Bev. | | 0.006* | 0.025* | 0.212 | 0.915 | 0.990 | 0.083 | | |
| | Ran. vs Afl. | | <0.001* | <0.001* | 0.004* | 0.023* | 0.068 | 0.876 | | |
| | Bev. vs Afl. | | 0.156 | 0.124 | 0.064 | 0.046* | 0.084 | 0.039* | | |
| Left Kidney | Ran. vs Bev. | | 0.006* | 0.025* | 0.212 | 0.915 | 0.990 | 0.083 | | |
| | Ran. vs Afl. | | <0.001* | <0.001* | 0.004* | 0.023* | 0.068 | 0.876 | | |
| | Bev. vs Afl. | | 0.156 | 0.124 | 0.064 | 0.046* | 0.084 | 0.039* | | |

TABLE 4-continued

Statistical summary between the 3 treatment groups.

| Organ | Comparison | Day 0 | Day 1 | Day 2 | Day 4 | Day 8 | Day 14 | Day 21 | Day 28 | Day 35 |
|---|---|---|---|---|---|---|---|---|---|---|
| Spleen | Ran. vs Bev. | | 0.852 | 0.410 | 0.800 | 0.558 | 0.024* | 0.178 | | |
| | Ran. vs Afl. | | 0.467 | 0.383 | 0.420 | 0.646 | 0.963 | 1.000 | | |
| | Bev. vs Afl. | | 0.779 | 0.986 | 0.784 | 0.987 | 0.035* | 0.178 | | |
| Bladder | Ran. vs Bev. | | 0.014* | 0.246 | 0.001* | 0.997 | 0.040* | 0.140 | | |
| | Ran. vs Afl. | | 0.036* | 0.413 | 0.183 | 0.273 | 0.434 | 1.000 | | |
| | Bev. vs Afl. | | 0.827 | 0.970 | 0.010* | 0.354 | 0.280 | 0.140 | | |
| Right Femur | Ran. vs Bev. | | 0.338 | 0.011* | <0.001* | <0.001* | 0.001* | 0.214 | | |
| | Ran. vs Afl. | | 0.428 | 0.982 | 0.082 | 0.789 | 0.595 | 1.000 | | |
| | Bev. vs Afl. | | 0.050 | 0.021* | <0.001* | <0.001* | <0.001* | 0.214 | | |
| Left Femur | Ran. vs Bev. | | 0.734 | <0.001* | <0.001* | <0.001* | 0.005* | 0.469 | | |
| | Ran. vs Afl. | | 0.221 | 0.283 | 0.002* | 0.777 | 1.000 | 1.000 | | |
| | Bev. vs Afl. | | 0.071 | 0.004* | 0.002* | <0.001* | 0.005* | 0.469 | | |
| Heart | Ran. vs Bev. | | <0.001* | <0.001* | <0.001* | <0.001* | <0.001* | 0.063 | | |
| | Ran. vs Afl. | | 0.459 | 0.078 | 0.013* | 0.395 | 0.900 | 1.000 | | |
| | Bev. vs Afl. | | <0.001* | <0.001* | <0.001* | <0.001* | <0.001* | 0.063 | | |
| Liver | Ran. vs Bev. | | <0.001* | <0.001* | 0.008* | <0.001* | 0.005* | 0.073 | | |
| | Ran. vs Afl. | | 0.846 | 0.017* | 0.132 | 0.339 | 0.681 | 1.000 | | |
| | Bev. vs Afl. | | <0.001* | <0.001* | <0.001* | <0.001* | 0.016* | 0.073 | | |

*indicates statistica significance (p < 0.05); blanks indicate no measurable radioactivity Table 4. Summary of the p-values adjusted for multiple comparisons between the 3 treatment groups at each time point and for each studied organ. In general, I-124 ranibizumab revealed significantly higher uptake in the renal system (kidneys and bladder) at the earlier time points (days 1 and 2). I-124 bevacizumab exhibited significantly higher uptake than both other agents in the heart, liver and distal femur bones throughout the study, and in the injected eye at the latter time points.

Radioactivity levels were not measurable in any of the organs after day 21 with the exception of the injected right eye and both thyroid lobules. Radioactivity measurements in the studied bilateral extraocular organs (thyroid, kidneys and distal femurs) revealed close correlation between the left and right sides at each time point. In general, I-124 bevacizumab was present in extraocular organs at higher levels in the later time points and was found to be significantly more disseminated in these organs compared to the other 2 agents. I-124 aflibercept and I-124 ranibizumab exhibited similar biodistribution patterns and were primarily found at earlier time points in excretory organs such as the urinary system (kidneys and bladder) and mononuclear phagocytic system (MPS, spleen). There was no accumulation found in the central nervous system for any of the labeled agents and there were no significant differences or trends found in the biodistribution of any of the studied extraocular organs between male and female subjects.

Injected and contralateral eye (FIG. 6). The injected right eyes did not display significant differences between the 3 labeled drugs during the first week after injection (days 0-8). Beginning on day 14, I-124 bevacizumab was found in significantly higher levels compared to both other agents. In the non-injected left eyes, all 3 labeled agents were visible on days 1, 2 and 4. I-124 bevacizumab was significantly higher than both other agents only at day 8, and all agents had very low levels of detection after day 8.

Thyroid gland (FIG. 6). Accumulation of I-124 in the thyroid gland was clearly visible at all of the time points beginning on day 1. No significant differences between the agents were found throughout the study. The three agents peaked at day 8 followed by gradually decreasing levels until day 35.

Urinary and mononuclear phagocytic systems (FIG. 7). I-124 ranibizumab was found at significantly higher levels in both kidneys and in the bladder on days 1 and 2 compared to both other agents. All 3 agents were clearly visible in the spleen on days 1, 2 and 4 without significant differences between them.

Other organs (FIG. 8). I-124 bevacizumab was visible at levels that were significantly higher compared to both other labeled agents at all measurable time points in the heart, liver and both distal femurs. For each of these organs, I-124 bevacizumab levels peaked at day 2 and then decreased gradually until disappearing after day 21.

In this investigation, I-124 bevacizumab was found to have a significantly longer half-life (3.60 days) compared to the two other labeled agents. Ranibizumab had a longer half-life (2.73 days) than aflibercept (2.44 days) that was not significantly different. The half-lives of the 3 labeled anti-VEGF agents in this study were found to be shorter than those in previously published reports on a rabbit model.4, 12 This is likely due to the liquefied nature of the vitreous found in adult owl monkey eyes and is consistent with the significantly faster clearances found in post-vitrectomized eyes in a rabbit model using similar PET methodology. There is scant literature on pharmacokinetic studies examining intravitreal ranibizumab and aflibercept on a primate model. One recent report by studied serial aqueous humor drug measurements in macaques after intravitreal injections with ranibizumab and aflibercept, and the half-lives were found to be 2.3 days for ranibizumab and 2.2 days for aflibercept, more similar to our results.

I-124 bevacizumab serum levels and pharmacokinetic parameters were significantly higher than both other agents and those of I-124 aflibercept were higher than I-124 ranibizumab. Gamma counter radioactivity levels rather than immunoassay methods were used to assess the labeled anti-VEGF agents in the serum. The trends in the serum found for each the 3 agents reflect similar differences with those reported in humans studying the same 3 agents.

Few studies have reported serum ranibizumab levels after intravitreal injection because they are either found at very low levels or are not measurable by 2 days after injection. To capture the earlier systemic clearance pattern previously reported for ranibizumab, this study included multiple early time points at 1, 2, 4, 8 and 12 hours after injection. The findings confirmed that after peaking in the serum 24 hours post-injection, ranibizumab was rapidly cleared from the bloodstream. Previous studies have examined VEGF serum levels following intravitreal anti-VEGF injection and have reported shorter duration and less VEGF suppression in the serum after ranibizumab intravitreal placement in comparison to both bevacizumab and aflibercept. Peripheral VEGF suppression has been found to be especially pronounced after intravitreal bevacizumab therapy in patients with retinopathy of prematurity.

Bevacizumab and aflibercept have an Fc-fragment that allow the agents to be engulfed by RPE cells and retinal endothelial cells. By contrast, ranibizumab lacks the Fc-fragment and is rapidly cleared from the circulation once the drug enters the bloodstream. Internalization of the Fc-containing agents may allow their physiologic effects to remain active after they are no longer detectable by PET imaging. It is uncertain whether the hybrid structure of aflibercept affects the duration of its intracellular captivity as reflected by the reduced half-lives within the vitreous and in the serum as compared to bevacizumab in this study and in other reports.

The accumulation of anti-VEGF agents in extra-ocular organs after intravitreal injection has not been previously examined and the clinical consequences of the dissemination patterns found in this study are uncertain. Previous studies on rabbits using the same methodology were performed using 1 bed acquisitions focusing on the head and neck. Although significant radioactive accumulations were reported in those studies, radioactivity in other extraocular organs below the neck would not have been detected. In clinical practice, ophthalmologists are often not aware of a patient's ongoing medical history and associations of systemic adverse events following intravitreal injection are likely to be underreported.

The side effects of systemic bevacizumab are well-known and include hypertension, proteinuria, wound dehiscence, incisional hernias, surgical site bleeding, GI perforation, non-ocular hemorrhages and thromboembolic events. Systemic side effects following intravitreal anti-VEGF therapy are less clear. A subset of patients including elderly patients, diabetics and ROP infants may be especially susceptible to systemic adverse events such as stroke, wound healing complications and death. A meta-analysis of CATT and IVAN clinical trials at the 2 year mark showed a significant increase in the risk of developing certain systemic side effects including gastrointestinal hemorrhages, hernias, nausea and vomiting with bevacizumab when compared to ranibizumab.

In a rabbit model, intravitreally placed bevacizumab was found to significantly delay cutaneous wound healing in a rabbit model. In the kidney, preglomerular, glomerular and peritubular endothelial cells are known to be VEGF-reliant. Several studies in the nephrology literature have reported the presence of renal complications following intravitreal anti-VEGF therapy including proteinuria and hypertension. Tschulakow et al. found that aflibercept and ranibizumab were both detected within glomerular capillaries after a single intravitreal injection of these agents in a cynomolgus primate model. Their findings are consistent with the rapid accumulation of ranibizumab in the kidneys following intravitreal injection found in this investigation.

There were several limitations in this study. First, peripheral organ uptake of I-124 labeled drugs after intravitreal injection is expected to be higher than that measured by PET because of decoupling between I-124 and the drug substrate. Once the I-124 labeled anti-VEGF agent exits the eye and becomes absorbed into the blood stream, an uncertain proportion of I-124 decouples from its substrate and becomes sequestered by the thyroid gland reducing the measured radioactivity in the peripheral organs. Since there were no significant differences found in the thyroid at any time point between the 3 agents, the amount of I-124 decoupling in the serum is likely to be proportional among the studied drugs.

Within the vitreous cavity, anti-VEGF agents are not known to be metabolized and the amount of decoupling is likely to be small. The clearance half-lives of previously reported intravitreal I-124 bevacizumab and I-124 ranibizumab measured by radioactive emission have compared favorably to pharmacokinetic reports using immunoassay methods in a similar rabbit model. Future studies are needed to quantify the proportion of I-124 that decouples from the drug substrate in the serum, and to perhaps mathematically factor in the decoupled proportion of I-124 into the radioactivity measurements for each of the studied organs. Second, the weight and size of an owl monkey is much smaller than that of an adult. The vitreous volume of the adult owl monkey varies between 2.0 and 2.5 mL as compared to approximately 4.5 mL in adult humans. They also have much smaller serum compartments than adult humans thus increasing their systemic exposure to humanly-dosed intravitreal drugs. The blood and plasma volumes in the owl monkeys are estimated to be 70 mL and 35 mL as compared to approximately 5 L and 2.6 L in human adults.

However, the liquefied vitreous found in this primate model may better simulate the intravitreal pharmacokinetic properties found in elderly adults with posterior vitreous detachment. Furthermore, the weight of an owl monkey and the size of its eye closely simulate those of a premature infant with retinopathy of prematurity (ROP), and the smaller serum size in the owl monkey model may more accurately represent the serum pharmacokinetic properties and biodistribution of intravitreally placed agents in these patients. Third, the use of a comparative methodology such as ELISA would have helped to verify serum measurements the radioactive decay of positron-emitting radionuclides is an inherently random process. Unfortunately, ELISA serum assay analysis was not available at our institution during the course of this project. Finally, studies with larger numbers of subjects per agent may further delineate the intravitreal pharmacokinetic patterns, serum characteristics and biodistribution uptakes of these agents, and may help to clarify whether or not the female-male differences in intravitreal retention rates of these drugs found in this investigation are significant.

In conclusion, the described methodology offers a novel approach for studying biodistribution and pharmacokinetic properties of radiolabeled intravitreally-placed therapeutic agents by serial PET/CT imaging of the same subject. I-124 bevacizumab had the longest intravitreal retention time and I-124 aflibercept the shortest. All three agents were found to be cleared through both the renal and mononuclear phagocytic systems. I-124 ranibizumab was rapidly cleared from the circulation while I-124 bevacizumab had significantly higher and prolonged levels in the serum, heart, liver and distal femur bones when compared to both I-124 ranibizumab and I-124 aflibercept.

Any PET-based imaging may be used in conjunction with the methods described herein. For example, PET/MRI in addition to PET/CT may be utilized.

While the embodiments and examples above describe various aspects of the inventive methods, they are not intended to limit same.

The invention claimed is:

1. A method for determining a systemic biodistribution of a radiolabeled intravitreally-placed medicament in a subject, the method comprising the steps of:
intraocularly placing a radiolabeled medicament including an anti-vascular endothelial growth factor (anti-VEGF) drug into the vitreous cavity of a subject's eye through the pars plana of the subject's eye; and
with a digital PET/CT (dPET/CT) apparatus, performing positron emission tomography (PET) imaging of radioactive emission of bodily parts that include the subject's eye and one or more of bladder, liver, heart, spleen, renal organs, and femur bones covered by a field-of-view of said dPET/PC apparatus, to quantify an uptake of said medicament containing the anti-VEGF drug systemically by said bodily parts to identify systemic side effects of the uptake of said medicament following the intraocularly placing.

2. The method of claim 1, wherein said performing PET imaging includes
imaging with said dPET/CT apparatus a systemic biodistribution of a drug including one or more of bevacizumab, ranibizumab, and aflibercept in said bladder, liver, heart, spleen, renal organs, and femur bones.

3. The method of claim 1, wherein said PET imaging is performed using a positron emission tomography/magnetic resonance imaging (PET/MRI) apparatus.

4. The method of claim 1, wherein said subject is a mammal.

5. The method of claim 1, wherein said subject is a non-human primate.

6. The method of claim 1, wherein said performing PET imaging includes performing serial imaging of non-ocular organs within the field-of-view of said dPET/CT apparatus.

7. A method for determining a biodistribution of a radiolabeled medicament containing an anti-vascular endothelial growth factor (anti-VEGF) drug in a subject, the method comprising the step of:
performing positron emission tomography (PET) imaging of radioactive emission of a subject's eye and one or more non-ocular organs within a field of view of a tomographer used for said imaging to identify systemic uptake of said anti-VGEF drug by the one or more non-ocular organs after intraocular placement of said radiolabeled medicament containing an anti-VEGF drug into the vitreous cavity of the subject's eye through the pars plana of the subject's eye.

8. The method of claim 7, wherein said PET imaging is performed using a high-resolution digital PET/CT (dPET/CT) apparatus having a field-of-view covering the subject's eye and said one or more non-ocular organs that include one or more of bladder, liver, heart, spleen, renal organs, and femur bones.

9. The method of claim 7, wherein said PET imaging is performed using a positron emission tomography/magnetic resonance imaging (PET/MRI) apparatus.

10. The method of claim 7, wherein said subject is a mammal.

11. The method of claim 7, wherein said subject is a non-human primate.

12. The method of claim 7, wherein said performing PET imaging includes performing serial imaging.

* * * * *